United States Patent [19]

Shiono

[11] Patent Number: 5,393,303
[45] Date of Patent: Feb. 28, 1995

[54] ATTACHMENT FOR LEG AND FOOT JOINT

[75] Inventor: Katsuaki Shiono, Hatogaya, Japan

[73] Assignee: Alcare Co., Ltd., Japan

[21] Appl. No.: 958,328

[22] PCT Filed: Apr. 17, 1992

[86] PCT No.: PCT/JP92/00489

§ 371 Date: Dec. 16, 1992

§ 102(e) Date: Dec. 16, 1992

[87] PCT Pub. No.: WO92/18072

PCT Pub. Date: Oct. 29, 1992

[30] Foreign Application Priority Data

Apr. 17, 1991 [JP] Japan .................. 3-035234

[51] Int. Cl.⁶ .............................................. A61F 5/00
[52] U.S. Cl. ........................................ 602/27; 602/23; 602/28
[58] Field of Search .................. 602/27, 23, 28, 29, 602/5, 62, 65

[56] References Cited

U.S. PATENT DOCUMENTS

| | | | |
|---|---|---|---|
| 3,073,305 | 1/1963 | Biggs, Jr. et al. | 602/65 |
| 4,166,460 | 9/1979 | Applegate | 602/65 X |
| 4,280,489 | 7/1981 | Johnson, Jr. | 128/80 |
| 4,287,920 | 9/1981 | Johnson, Jr. | 141/85 |
| 4,771,768 | 9/1988 | Crispin | 602/27 X |
| 4,825,856 | 5/1989 | Nelson | 602/27 |
| 5,007,416 | 4/1991 | Burns et al. | 602/27 |
| 5,038,762 | 8/1991 | Hess et al. | 128/80 |
| 5,094,232 | 3/1992 | Harris et al. | 602/27 X |
| 5,099,860 | 3/1992 | Amrein | 602/27 X |
| 5,113,877 | 5/1992 | Johnson, Jr. et al. | 602/27 X |
| 5,217,431 | 6/1993 | Toronto et al. | 602/27 |

FOREIGN PATENT DOCUMENTS 2182252 7/1990 Japan .

Primary Examiner—Richard J. Apley
Assistant Examiner—Linda C. M. Dvorak
Attorney, Agent, or Firm—Haverstock, Garrett & Roberts

[57] ABSTRACT

An ankle brace to be used for therapy and prevention of orthopedic injuries in the ankle joint area, the ankle brace is comprised of a main brace body (1) having a shank or lower leg covering portion (2) and a foot covering portion (4), an inner stay (22) and an outer stay (23) which are each detachably mounted, and a coupling or connecting belt (24) for connecting the two stays together. The lower leg covering portion (2) is able to be opened and closed at its front side through the use of surface fasteners (9 and 10) and includes a plurality of fastening belts (15 to 18). The foot covering portion (4) is coupled or connected to the lower end of the lower leg covering portion (2) and is able to be opened and closed at its front side through the use of a surface fastener (12) and is provided with at least one stretchable belt (20, 21). The main brace body (1) includes an opening (13) into which the heel of a foot can be inserted, and the inner stay (22) and outer stay (23) are each adaptable to be attached to and detached from the side faces of the main brace body (1). The construction of the ankle brace is such that it is easy to put on; it has high stability during wear; and it is able to be adjusted according to conditions in each step of the healing process so as to provide an optimum remedial function for the particular therapeutic purpose.

12 Claims, 4 Drawing Sheets

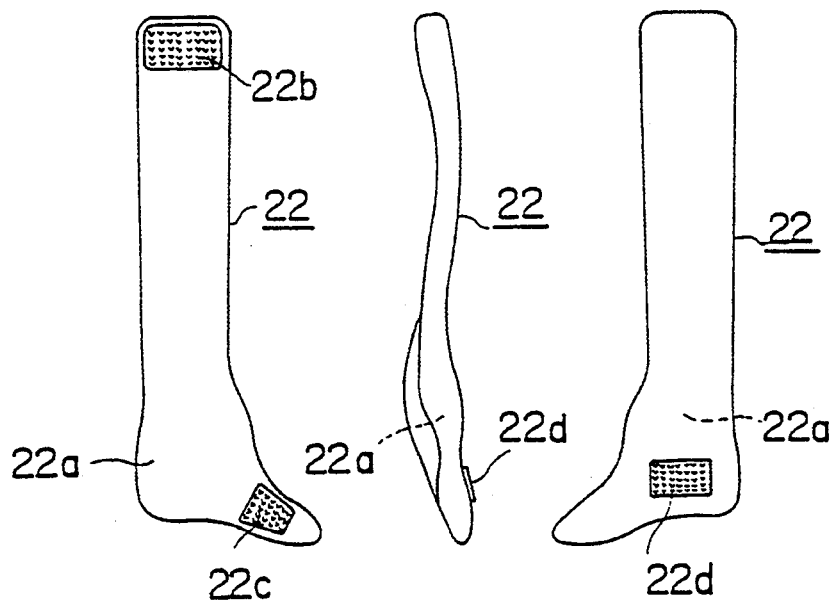
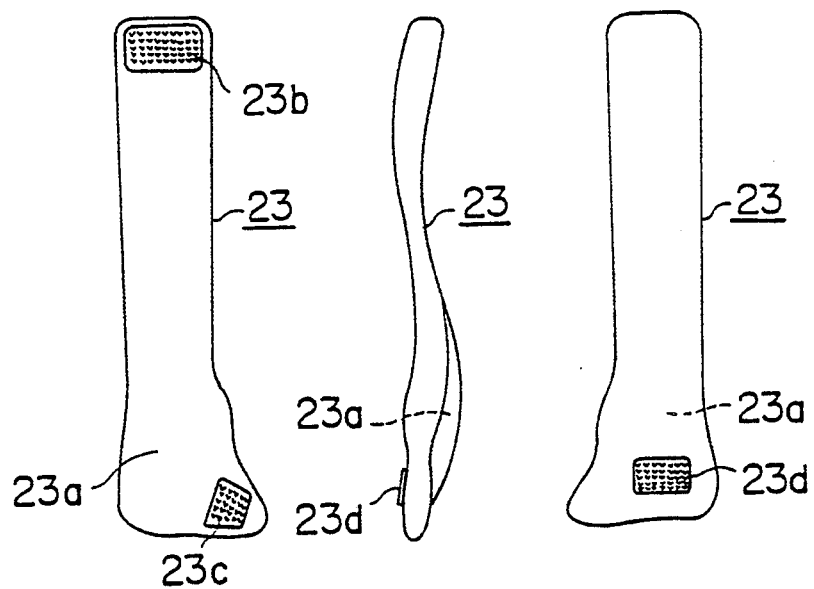

ATTACHMENT FOR LEG AND FOOT JOINT

Applicant hereby claims foreign priority benefits under 35 USC § 119 of corresponding Japanese Utility Model Application No. (Hei) 3-35234, filed Apr. 17, 1991, and Japanese PCT patent application Serial No. PCT/JP92/00489, filed Apr. 17, 1992.

BACKGROUND OF THE INVENTION

TECHNICAL FIELD

The present invention relates to an ankle brace which fixes and supports that portion of the leg and foot of a patient extending from the lower leg or shank portion to the foot for the purpose of providing medical treatment or preventing orthopedic problems pertaining to the bones, ligaments and so forth of the ankle joint. The fixation force applied by the brace can be adjusted in accordance with the degree necessary to treat a particular disorder and/or heal the same.

TECHNICAL BACKGROUND

Of all the injuries giving rise to ankle joint pain, those which are experienced most frequently are sprains to the ankle joints. There are however various degrees of sprains extending from the simple sprain of a ligament to the rupture of a ligament accompanied by no avulsion of the bone to which the ligament attaches. Moreover, among the injuries to the ankle joint, the most serious ones are dislocation fractures. These injuries include various degrees of injury extending from such a degree of injury that the stability of the ankle joint is not affected to such a degree of injury that the ankle joint becomes seriously unstable. In case of a slight sprain of the ankle joint ligament, the range of motion of the inversion or eversion does not exceed the normal range but, in case of a serious sprain, the range of motion exceeds the normal range and, in case of a more serious sprain, even a drawer sign appears.

As for the method of treatment for these injuries, an elastic bandage, an adhesive tape, a supporter or the like is usually applied onto the ankle joint portion when the injury is slight so that, in daily life, a large burden is not placed on the ankle joint and, thus, the patient can make nimble movements.

In the case of a medium degree injury, pain or instability is caused in the ankle joint and, therefore, it is necessary to control the lateral sway, plantar flexion, dorsiflexion, adduction or abduction of the ankle joint. For the treatment of such injuries, a splint is applied to the ankle joint and fixed thereto by use of an elastic bandage. A neoprene supporter composed of stretch fabrics having a neoprene sponge held therebetween, or a plastic sheet-incorporated neoprene supporter composed by sewing plastic sheet-like L-shaped plates to both sides of the above-mentioned neoprene supporter may be applied. Similarly, a U-shaped brace as disclosed in U.S. Pat. Nos. 4,280,489 and 4,287,920 may also be used, the brace being constructed in such a manner that plastic plates are applied to both sides of the leg extending from the lower leg portion or shank to the heel of the foot, the width of the heel portion being adjusted by use of a Velcro or surface fastener, the lower leg portion being clamped and fixed at a suitable position by use of a surface fastener such as a VELCRO fastener after the appliance is mounted. Further, there has also been proposed an ankle brace constructed in such a manner that, to the neoprene supporter or the plastic sheet-incorporated neoprene supporter, a cross belt is mounted, the cross belt comprising a stretch belt which is extended from the sole portion or a side face of the foot so as to pass the instep of the foot and which can be spirally wound upwardly towards the lower leg in order to prevent the occurrance of an inversion or an eversion, the ankle brace being adapted to be either open in the front or in the rear in order to both facilitate the attachment of the brace to the ankle and to enhance its overall fitness.

Still further, there has been proposed an ankle joint splint (See Japanese Unexamined Patent Application Publication No. Hei 2-182252) constructed in such a manner that an outer plate is placed upright along the side face in front of the malleolus, and an inner plate is placed upright in front of the achilles tendon in opposed relationship to the outer plate, both plates extending upwardly from the web reaching the front portion of the heel in parallel along the side faces of both sides of the bones of the lower leg. Holding straps are attached to the lower end portion of the respective plates on both sides thereof so that they extend from one of the plates passing the instep of the foot in an obliquely upward direction and are of sufficient length to reach the other plate, at which point the straps are fixed. The straps are then passed around the achilles tendon above the malleolus and are made to cross each other on the instep and are thereafter fixed to a stopper on the other plate.

The above-mentioned ankle braces can play an auxiliary role to some degree in the case of a slight injury and thus are useful for therapy only during a specific portion of the therapeutic process. These braces are not suited for use in the therapeutically necessary periods both before and after the specific therapeutic period for which they are used. Furthermore, in the case of a medium degree injury, or in case of an injury which must be protected with a sure fixation force as in the case of fixation of an injury after the operation thereof, such braces cannot be used. Moreover, an injury pertaining to the ankle joint is liable to relapse and, therefore, such an injury must be perfectly cured in the therapeutical stage. However, for that purpose, it is necessary to perform rehabilitation of the patient and take a preventative measure to gradually enhance the function of the ligament of the ankle joint in step with the therapeutic process. A device which can satisfy the above-mentioned requirements has not yet been realized.

SUMMARY OF THE INVENTION

It is the object of the present invention to provide an ankle brace constructed in such a manner that the ankle brace can be easily applied, its stability while being worn by a patient is high and, in addition, it can be adjusted so that the brace can provide an optimum remedial function for the intended therapeutic purpose in accordance with each step of the therapeutic process.

In order to achieve the above-mentioned purpose, the ankle brace according to the present invention comprises a main brace body having a lower leg or shank covering portion which covers the leg between the knee and the ankle, a foot covering portion which covers the foot portion, an inside and an outside stay which are each detachably mounted onto the surfaces on both sides of the main brace body, and a coupling or connecting belt for connecting the stays together. The lower leg covering portion is comprised of a material which has elasticity, stiffness and stretchability, and which can be opened and closed at the front portion thereof by means of surface fasteners such as Velcro fasteners, and includes a plurality of binding belts which extend approximately horizontally so as to be wound respectively around the lower leg portion. The foot covering portion is coupled with the lower end of the lower leg covering portion in such a manner so as to extend approximately perpendicular to the lower leg covering portion, the foot covering portion being freely opened or closed on the dorsal surface portion of the foot by means of a surface fastener such as a VELCRO fastener. The foot covering portion includes at least one stretchable belt, one end of which is fixed to the outer surface of the plantar surface portion thereof and extends from the foot plantar surface portion over the dorsal surface portion of the foot and can be spirally wound around the lower leg portion of the present brace, the other end of the stretchable belt including a surface fastener such as a VELCRO fastener for fastening itself onto the lower leg covering portion.

The main brace body includes an opening in the portion thereof where the lower leg covering portion and the foot covering portion meet and are connected together. The inside stay and the outside stay are each composed of a highly rigid material, the inside stay having a curved surface corresponding to the inside face of a patient's leg extending from the lower leg portion to the foot portion and being somewhat L-shaped, while the outside stay has a similar curved surface corresponding to the outside face of a patient's leg extending from the lower leg portion to the foot portion and is likewise somewhat L-shaped, the two stays having on their respective internal sides a plurality of surface fasteners such as Velcro fasteners for attaching or detaching such fasteners to and from the surface of the main brace body. The two stays each further include a surface fastener such as a Velcro fastener on the lower end portion of their respective external sides for connecting together the two stays.

According to the present invention, the heel of a patient is inserted into the opening of the main brace body formed between the foot and lower leg portions, and this correctly determines the proper orientation of the main brace body for attachment to the leg. The front portions of the foot covering portion are now overlapped onto the dorsal surface of the foot and coupled together by means of surface fasteners such as VELCRO fasteners associated therewith and this fixes the foot covering portion to the foot portion of the patient. The opposite end front portions of the lower leg covering portion are now overlapped onto the lower leg portion of the patient and are likewise coupled together by means of surface fasteners such as VELCRO fasteners. This initially fixes the lower leg or shank covering portion to the lower leg portion of the patient and, by winding and fixing the clamping belts associated with the lower leg covering portion of the brace, the lower leg covering portion is held in a proper position with a greater sureness. Furthermore, by wrapping the stretchable belt associated with the foot covering portion around the ankle and lower leg portion so as to extend up to and engage the upper portion of the lower leg, the inversion or eversion of the ankle joint can be prevented. Moreover, virus and valgus instability, plantar flexion and dorsal flexion can be limited through use of the stays and, by increasing or decreasing the fixation force of the stretchable belts and by varying the number of stays utilized, various different support forces can be obtained.

According to the present invention, the inside stay and the outside stay are each independently detachably mounted to the main brace body and, therefore, optimum fixation methods can be selected in accordance with the various injuries of the ankle joint, the degree of the injury and the curing states required for the healing thereof. As a result of the present ankle brace, it is not necessary to keep in stock a number of different kinds of braces for different types of injuries to the ankle joint and, for each step during the curing or convalescence stage, it is not necessary to purchase a new brace. Thus, according to the present invention, an economical and timely therapy can be carried out, which leads to an early cure of the injury.

Moreover, the inside and outside stays according to the present invention have sufficient widths and curved surfaces conformed to the side faces of the lower leg and foot portions of the patient's leg such that various motions of the foot such as an inversion, an eversion, a plantar flexion, a dorsal flexion and so forth are wrapped in by the curved surfaces of the stays and thus a sure fixation force can be obtained.

The foot covering portion according to the present invention has an opening in the heel portion thereof into which the heel of a patient can be deeply inserted and, when so inserted, the foot covering portion of the present brace fits into the plantar arch portion of the foot so that, during the wearing of the present ankle brace, the foot covering portion is not shifted forwardly or backwardly, whatever movement may be made, and thus can be fixedly held at the correct position without fail. Moreover, the foot covering portion does not cover the toe joints of the foot so that, even when the patient wears the ankle brace, walking is not affected. Still further, since the present construction precludes the application of any unnecessary fixation force when applied and worn, there is no possibility of joint arthrokleisis, amyotrophy of the muscle and so forth and thus, the curing process can be shortened.

The lower leg or shank covering portion according to the present invention can cover even such a portion of the leg as the sura or calf portion of the leg so that, during walking, the lower leg covering portion will not slip down. Moreover, since one or more stretchable belts are used, it is ensured that, by adjusting the tensile force thereof, the direction of an inversion or eversion of the foot can freely be restricted.

As stated above, the ankle brace according to the present invention is constructed in such a manner that adjustment can be made so as to produce an optimum fixation force in accordance with each step of the curing stage and, in addition, the mounting of the ankle brace is very easy and its stability during use is very excellent.

BRIEF DESCRIPTION OF THE DRAWINGS

FIGS. 3(a), 3(b) and 3(c) represent a left-side view, a front view, and a right-side view respectively of the inside stay constructed according to the present invention;

FIGS. 4(a), 4(b) and 4(c) represent a left-side view, a front view, and a right-side view respectively of the outside stay constructed according to the present invention;

FIG. 5 is a front view of the stay coupling belt constructed according to the present invention.

PREFERRED EMBODIMENT OF THE INVENTION

An embodiment of the present invention will now be described by reference to the drawings.

Figure 1:
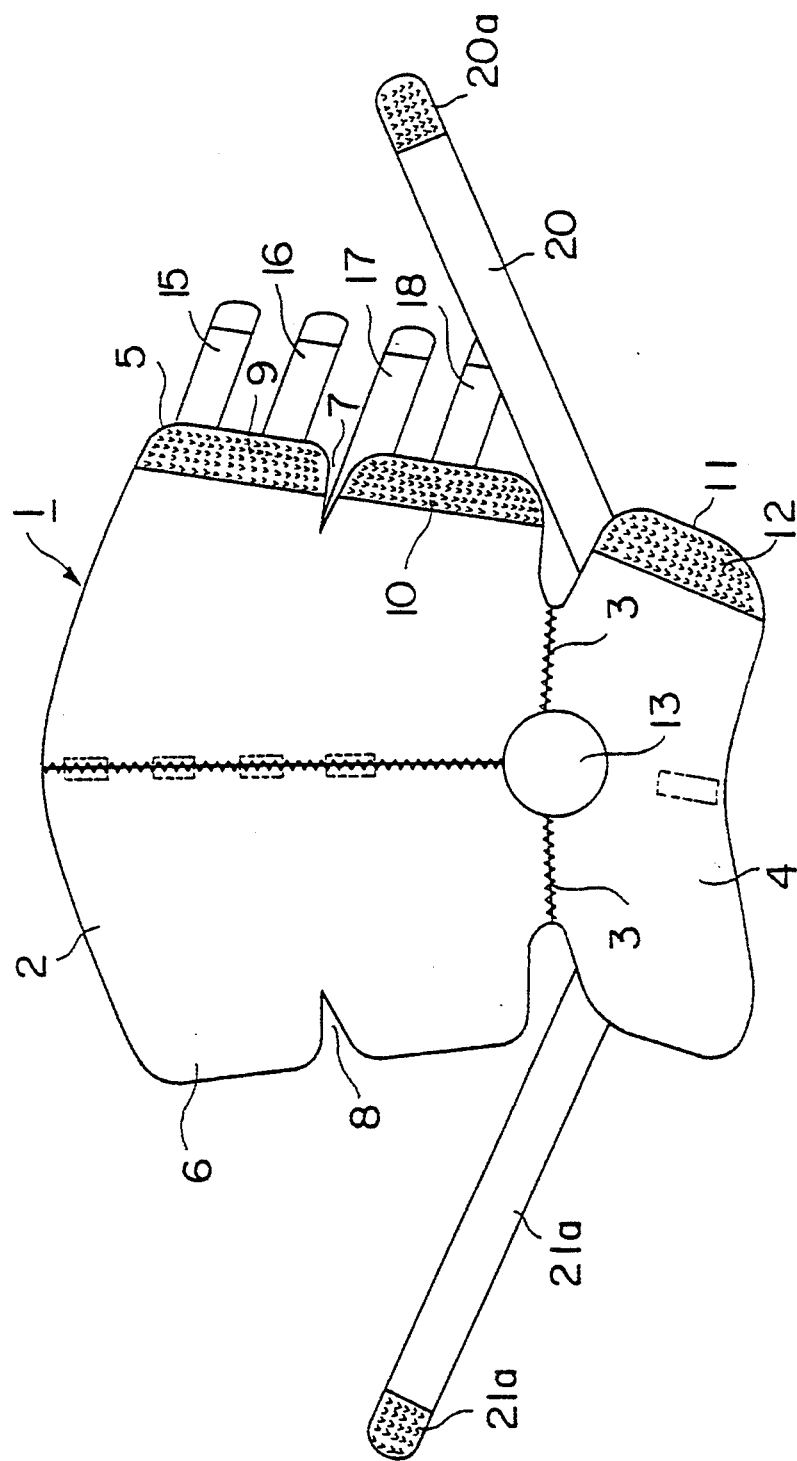
FIG. 1 is a front view of an embodiment of the present invention.
Figure 2:
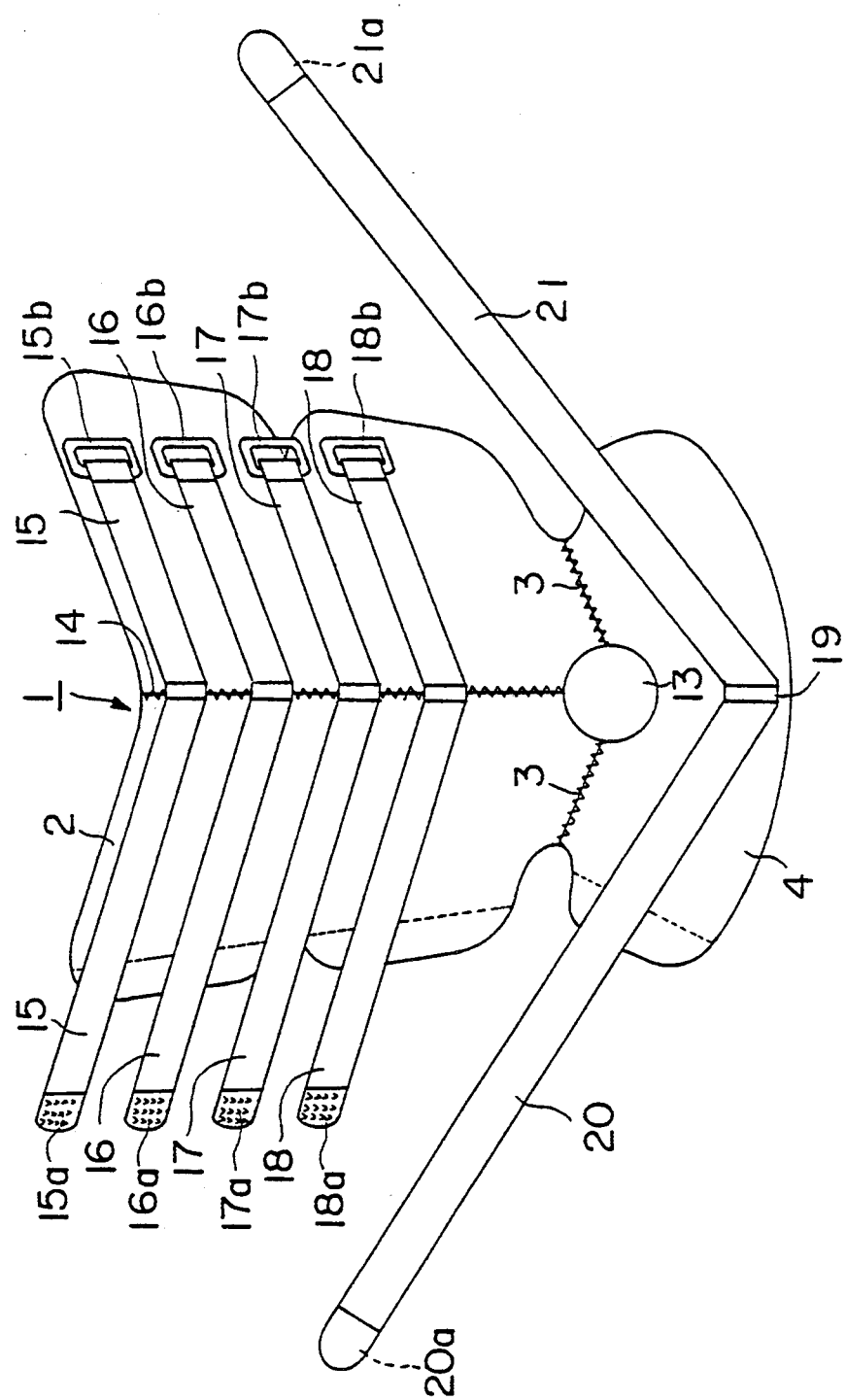
FIG. 2 is a rear view of the embodiment of the present invention shown in FIG. 1.

Referring to FIGS. 1 and 2, numeral 1 denotes a main brace body comprising a lower leg or shank covering portion 2 which covers that portion of the leg extending from nearly the sura or calf portion of the lower leg to the upper portion of the heel, and a foot covering portion 4 which is connected to the lower leg covering portion 2 along the edge portion 3 on both the inside and outside portion of the ankle joint and covers that portion of the foot extending to the vicinity of the metatarsus bone. The lower leg covering portion 2 is formed of a cloth having a width and length sufficient to cover that portion of the leg extending from the sura portion of the lower leg to the upper portion of the heel. The two sides 5 and 6 of the lower leg covering portion 2 include notches 7 and 8 respectively so as to divide each of the two sides into two portions. On the inner surface of one side portion 5, surface fasteners 9 and 10 in the form of VELCRO fasteners or other similar materials which adhere when pressed together are provided so that the front open portions of the lower leg portion 2 can be closely attached, with ease, to the corresponding surface of the lower leg side portion 6 with a slight force, yet with sureness. In the embodiment shown, the two sides of the lower leg covering portion 2 are each divided into two portions respectively, but the number of divisions is not necessarily limited to two. Depending upon the length of a patient's leg, the number of divisions can be suitably altered to obtain such a width of the lower leg covering portion as to allow the brace to be carried easily by hand.

The foot covering portion 4 is of a width and length sufficient to cover that portion of the foot extending from the heel to the vicinity of the metatarsus bone and is of such an overlapping structure that the side end portions thereof can be closed and opened on the dorsal surface of the foot. On one side 11 of the foot covering portion 4, a surface fastener 12 in the form of another VELCRO fastener is provided. Moreover, along the coupling edge portion 3 between the lower leg covering portion 2 and the foot covering portion 4, there is also provided an opening 13 into which more than about half of the heel of a patient can be inserted.

The main brace body 1 is composed of a material which is flexible, elastic, stiff and stretchable; it is high in backstretch; it does not deform even if used for a long period; it is washable; and it does not become hot and stuffy while in used. As the core material for the main brace body 1, for example, a non-woven fabric composed of polyurethane, styrene-isoprene styrene, a synthetic or natural rubber foam such as urethane, neoprene or the like, may be used. For the inner side (rear surface) of the main brace body 1, a tricot or stretch fabric which is knitted from cotton, polyester, polyamide, polyacryl, etc. may be used; and, for the outer side (front surface) of the main brace body 1, a stretch French pile which can be fastened to a VELCRO fastener strip comprised of polyester, polyamide or the like may be used. Thus, the main brace body 1 can be composed of a fabric comprised of a laminated three-layer structure. Particularly preferable is a laminated three-layer structure material obtained by use of a polyurethane non-woven fabric having a weight-per-unit-area of 200 g as the core material, a sweat-in and sweat-out type polyester fabric with the trade name of "Control" (manufactured by Asahi Chemical Industry Co., Ltd.) or "Field Sensor" (manufactured by Toray Industries, Inc.) as the inner layer, and a polyamide series stretch French pile as the outer layer.

At approximately the center rear surface portion 14 (FIG. 2) of the lower leg covering portion 2 corresponding to the calf portion, four binding belts 15, 16, 17 and 18 are coupled or attached thereto at approximately equal intervals therebetween extending from the upper to the lower portion of the lower leg portion 2 as shown in FIG. 2 in such a manner as to extend to the right and left as shown. These binding belts 15-18 are of a length sufficient to be wound around the shank portion 2 and each includes a VELCRO fastener strip 15a-18a respectively on one-end portion thereof, while, at the respective opposite ends thereof, rings 15b-18b are mounted so that the respective end portions 15a-18a of the belts 15-18 can be inserted through the corresponding rings 15b-18b respectively and thereafter turned back unto themselves so as to allow the VELCRO fasteners 15a-18a to be securely fixed onto the surfaces of the respective belts. The width of each of the binding belts 15-18 should desirably be about 50 mm. For the material comprising such binding belts, a non-stretchable or stretch retardant cloth such as cotton belts, or nylon belts may be used and, desirably, such belts each include on one side surface thereof a pile with which the VELCRO fastener strips will adhere to when pressed together.

Figure 6A:
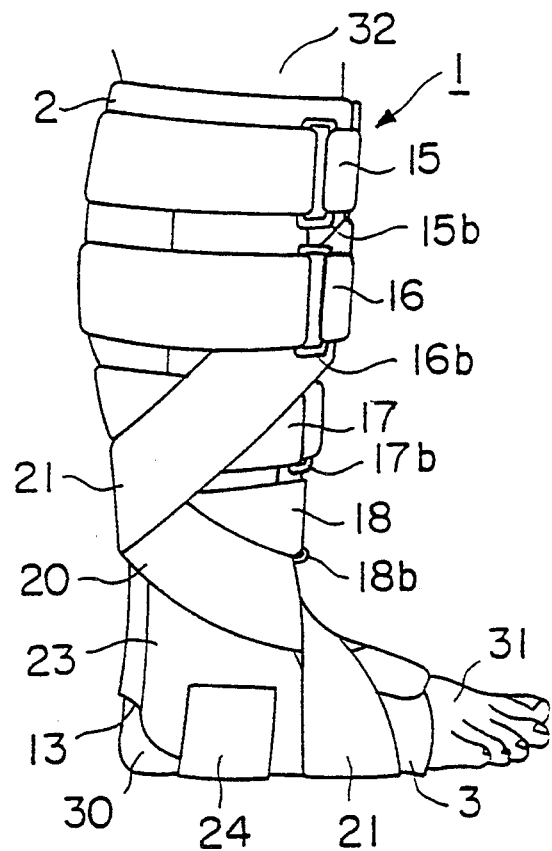
FIGS. 6(a) and 6(b) represent a side view and a front view respectively showing the ankle brace of the present invention attached to the leg and foot of a patient.
Figure 6B:
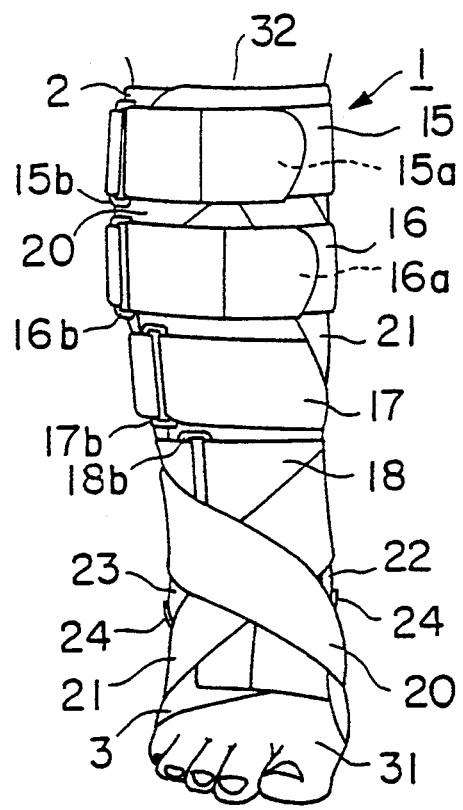

To a center rear portion 19 of the outer surface of the foot covering portion 4, stretch belts 20 and 21 which extend obliquely in the right and left directions as shown in FIG. 2 are connected thereto and each has a length sufficient to ensure that, when the ankle brace is mounted on the patient, the stretch belts 20 and 21 extend from the plantar surface portion of the foot, pass the dorsal surface portion, and extend round the back portion of the lower part of the lower leg covering portion 2 so as to reach the upper portion thereof. The stretch belts 20 and 21 likewise include surface fasteners 20a and 21a such as VELCRO fasteners at the respective end portions thereof. These stretch belts 20 and 21 should desirably be 30 mm to 70 mm in width and can be comprised, for instance, of rubber-woven bands, power nets or the like. In the drawings, there are shown two stretch belts 20 and 21 which extend towards both sides from the plantar portion of the foot and cross each other as shown in FIGS. 6(a) and 6(b). However, it is not necessary that only two such belts be used as any number of belts may be utilized, and even one such belt will suffice.

Referring to FIGS. 3 and 4, an inside stay 22 and an outside stay 23 are each molded-stays formed in conformity with the shapes of the internal and external sides of the portion of the leg extending from the shank to the foot portion via the ankle joint. These stays 22 and 23 can be formed by a method such as hot-press-forming, vacuum forming, or injection molding of a thermoplastic resin such as ABS resin, polymethyl methacrylate resin, polyester resin, polycarbonate resin, polyamide resin, polyvinyl chloride resin, transform polyisoprene resin, ionomer resin or the like. The thickness of the stays 22 and 23 should desirably be 1 mm to 8 mm in view of the desired strength and the width of the stays should desirably be 30 mm to 100 mm in view of both the strength and the requirement that the stays have curved surfaces which can somewhat cover the side face of the leg portion extending from the shank to the foot portion. Furthermore, the peripheral portions of the two stays each have a suitable roundness so as to give a comfortable feeling to the skin, and portions 22a and 23a corresponding to the medial malleolus and lateral malleolus are largely depressed so as not to contact the medial malleolus and lateral malleolus.

Since the inside stay 22 and the outside stay 23 are combined with the surface of the main brace body 1, surface fasteners in the form of VELCRO fasteners 22b and 22c, 23b and 23c are provided on the upper and lower portions of the inner sides (rear sides) thereof. The number of these surface fasteners is not limited to two. Moreover, onto the inner sides of the stays 22 and 23, a cushioning material such as felt, polyurethane foam or the like, with a suitable thickness (about 0.5 mm–5 mm), may be applied.

Still further, on the outer surfaces of those portions of the inside and outside stays 22 and 23 which face the heel portion, surface fasteners such as VELCRO fasteners 22d and 23d are mounted so that the distance between the two stays can be adjusted when they are mounted to the main brace body 1, the two surface fasteners 22d and 23d being coupled or connected together through use of the coupling belt 24 shown in FIG. 5. The coupling belt 24 is composed of a nonstretchable or a stretch retardant material and, on one surface 24a thereof, there is provided a pile to which the surface fasteners 22d and 23d can be fasten.

The manner or method for applying the ankle brace according to the present invention will now be described by reference to FIGS. 6(a) and 6(b).

The present ankle brace is applied to the leg as follows. The inside and outside stays 22 and 23 are first separated from the main brace body 1, and the heel 30 of the patient is inserted sufficiently deep into the hole or opening 13 of the main brace body 1. The main brace body 1 is now made to fit or conform to the leg and foot as follows. The foot covering portion 4 is first sufficiently pulled out, overlapped and fixed over the foot 31 so as to cover the same as shown, and the opening/closing parts of foot covering portion 4 are fastened together by means of the surface fastener 12. Subsequently, the lower leg covering portion 2 is wound around the shank or lower leg portion 32 and the surface fasteners 9 and 10 are fastened gradually from the lower part to the upper part of the leg portion 32 whereby the leg portion 32 is covered and fixed by the brace covering portion 2. Next, the inside and outside stays 22 and 23 are applied to the leg over the brace portions 2 and 4 in such a manner that the portions 22a and 23a where depressions are provided are placed onto the medial malleolus and the lateral malleolus. The inside and outside stays 22 and 23 are then fixed to the positions of the internal side and external side of the leg and foot portions of the main brace body 1 by means of the surface fasteners 22b and 22c, 23b and 23c. Subsequently, the coupling belt 24 is passed from the plantar surface of the foot up to both opposite sides thereof as shown in FIGS. 6(a) and 6(b) and fastened to the surface fastener 22d of the inside stay 22 and the fastener 23d of the outside stay 23 whereby the two stays 22 and 23 are held in their correct positions respectively. Next, the binding belts 17 and 18 in the lower portion of the lower leg covering portion 2 are wound around the lower leg portion respectively and the tip ends of the respective surface fasteners 17a and 18a are passed through the rings 17b and 18b and turned back unto themselves so that the belts are bound and fixed by means of the fasteners 17a and 18a. Thereafter, the stretch belts 20 and 21 provided on the foot covering portion 4 are stretched from the plantar surface portion of the foot and passed over the back portion of the ankle joint one by one in conformity with the injury, and they are then wound around the lower part of the leg calf and extended spirally upwards over belts 17 and 18 as shown. These belts are then fixed to the surface of the lower leg covering portion 2 of the main brace body 1 above belts 17 and 18 by means of the surface fasteners 20a and 21a. Finally, the upper binding belts 15 and 16 of the lower leg covering portion 2 are wound around the stretch belts 20 and 21, and the tip ends of the respective surface fasteners 15a and 16a are passed through the rings 15a and 16a and turned back unto themselves whereby the belts 15 and 16 are bound and fixed by means of the surface fasteners 15a and 16a. This completes the wearing or mounting of the present ankle brace.

Further, in a case where one or both of the stays 22 and 23 are removed in accordance with the nature of the injury or the therapeutic process involved for healing the same, the present ankle brace can be applied in the same manner as mentioned above with exclusion of the mounting operation pertaining to the particular stays.

Thus, there has been shown and described novel means for an ankle brace for attachment to and around the leg and foot joint, which invention fulfills all the objects and advantages set forth above. It will be apparent to those skilled in the art, however, that many changes, modifications, variations and other uses and applications of the present invention are possible. All such changes, modifications, variations and other uses and applications which do not depart from the spirit and scope of the invention are deemed to be covered by the invention which is limited only the claims which follow.

What is claimed is:

1. An ankle brace for attachment to the leg and foot portion of a user so as to encompass the ankle joint comprising a lower leg covering portion, a foot covering portion, and a pair of L-shaped stay support members of rigid construction, said lower leg covering portion having inner and outer surface portions and being formed in such a manner so as to be wrappable around the lower leg of the user, said lower leg covering portion including means for holding and securing the same in proper position to the lower leg of the user, said foot covering portion having inner and outer surface portions and being attached to said lower leg covering portion, said foot covering portion being of a length and width sufficient to cover a portion of the foot extending from the heel to the vicinity of the metatarsus bone and being formed in such a maimer so as to be wrappable about the foot of the user, said foot covering portion further including means for enabling said foot covering portion to be held in proper position about the foot of the user and to be opened and closed on the dorsal surface portion of the foot, an opening formed in the area where said foot covering portion is attached to said lower leg covering portion, said opening being dimensioned so as to enable the heel portion of the foot of the user to be at least partially inserted therewithin, each of said L-shaped stay support members having inner and outer surface portions and each including an elongated portion adapted to extend along one side surface portion of the lower leg portion of the user and an extension portion extending outwardly from the elongated portion adapted to extend along the adjoining side surface portion of the foot, one of said stay support members being formed and dimensioned so as to correspond to the shape of the inside surface portion of the lower leg and foot of the user, the other of said stay support members being shaped and dimensioned so as to correspond to the shape of the outer surface portion of the lower leg and foot of the user, each of said stay support members including attachment means on the inner surface portions of the elongated portion and extension portion thereof for attaching said stay support member to both said lower leg covering portion and said foot covering portion so as to prevent relative movement between the lower leg portion and foot portion of the user.

2. The ankle brace defined in claim 1 including means for coupling said pair of stay support members together when positioned adjacent the respective inner and outer surface portions of the lower leg and foot of the user.

3. The ankle brace defined in claim 1 wherein said means for holding and securing the lower leg covering portion in proper position to the lower leg of the user includes cooperatively engageable fastening means associated with said lower leg covering portion, said cooperatively engageable fastening means being positioned and located so as to enable said lower leg covering portion to be wrapped around the lower leg of the user in overlapping fashion when engaged with each other.

4. The ankle brace defined in claim 3 wherein said means for holding and securing said lower leg covering portion around the lower leg of the user further includes a plurality of fastening belts attached to the outer surface portion of said lower leg covering portion, said plurality of fastening belts extending around the lower leg of the user and over said pair of stay support members when said fastening belts are respectively engaged with each other.

5. The ankle brace defined in claim 1 wherein said means for holding said foot covering portion in proper position about the foot of the user includes cooperatively engageable fastening means associated with said foot covering portion, said cooperatively engageable fastening means being positioned and located so as to enable said foot covering portion to be wrapped around the foot of the user in overlapping fashion when engaged with each other.

6. The ankle brace defined in claim 5 wherein said means for holding said foot covering portion around the foot of the user further includes at least one strap member having one end portion thereof fixed to the outer surface portion of said foot covering portion, said strap member being spirally wrappable around the lower leg portion of the user, the opposite end portion of said strap member having fastening means associated therewith attachable to corresponding means located on said lower leg covering portion for securing the same thereto.

7. The ankle brace defined in claim 2 wherein said coupling means includes a strap member, said strap member having means associated therewith cooperatively engageable with means associated with the outer surface portion of each of said pair of stay support members for coupling said stay support members together.

8. An ankle brace for attachment to the leg and foot portion of a user so as to encompass the ankle joint comprising a main brace body having a lower leg covering portion and a foot covering portion, an inside stay support member positionable adjacent the inside surface portion of the lower leg and foot of the user, an outside stay support member positionable adjacent the outside surface portion of the lower leg and foot of the user, and coupling means for connecting together the inside and outside stay support members when positioned adjacent the respective inside and outside surface portions of the lower leg and foot of the user, said lower leg covering portion having inner and outer surface portions and being formed in such a manner so as to be wrappable around the lower leg of the user, said lower leg covering portion including fastening means for holding and securing the same to the lower leg of the user when positioned therearound, said fastening means enabling said lower leg covering portion to be opened and closed on the front face portion of the lower leg of the user when wrapped therearound, said lower leg covering portion further including a plurality of strap members attached to the outer surface portion thereof, said plurality of strap members being adapted to extend around the lower leg of the user and including additional means for fastening the same therearound, said foot covering portion having inner and outer surface portions and being connected to said lower leg covering portion, said foot covering portion being formed in such a manner so as to be wrappable about the foot of the user and being of sufficient length and width to cover that portion of the foot extending from the heel to the vicinity of the metatarsus bone, said foot covering portion including fastening means for holding and securing the same to the foot of the user when positioned therearound, said fastening means enabling said foot covering portion to be opened and closed on the dorsal surface portion of the foot of the user when wrapped therearound, said foot covering portion further including at least one strap member spirally wrappable around the lower leg of the user, said strap member having opposite end portions, one end portion of said strap member being fixed to the outer surface portion of said foot covering portion, and the opposite end portion of said strap member having attachment means associated therewith attachable to corresponding means located on said lower leg covering portion for securing the same thereto, an opening formed in said main brace body in an area where said foot covering portion is connected to said lower leg covering portion, said opening being dimensioned so as to enable the heel portion of the foot of the user to be at least partially inserted therewithin, said inside stay support member having inner and outer surface portions and being L-shaped in form including an elongated portion adapted to extend along the inner side surface portion of the lower leg portion of the user and an extension portion extending outwardly from the elongated portion adapted to extend along at least a portion of the adjoining inner side surface portion of the foot, said inside stay support member being of rigid construction and formed and dimensioned so as to correspond to the inner curved surface of the lower leg and foot of the user, fastening means on the inner surface portions of the elongated portion and extension portion of said inside stay support member for independently removably attaching said member to the lower leg covering portion and the foot covering portion of said main brace body, said fastening means being cooperatively engageable with corresponding means located on the lower leg covering portion and the foot covering portion of said main brace body for holding said inside stay support member in position adjacent thereto, said outside stay support member having inner and outer surface portions and being L-shaped in form including an elongated portion adapted to extend along the outer side surface portion of the lower leg portion of the user and an extension portion extending outwardly from the elongated portion adapted to extend along at least a portion of the adjoining outer side surface portion of the foot, said outside stay support member being of rigid construction and formed and dimensioned so as to correspond to the outer curved surface of the lower leg and foot of the user, fastening means on with the inner surface portions of the elongated portion and extension portion of said outside stay support member for independently removably attaching said member to the lower leg covering portion and the foot covering portion of said main brace body, said fastening means being cooperatively engageable with corresponding means located on the lower leg covering portion and the foot covering portion of said main brace body for holding said outside stay support member in position adjacent thereto, said inside and outside stay support members when fastened to the lower leg covering portion and foot covering portion of said main brace body acting to prevent relative movement between the lower leg portion and foot portion of the user, and each of said stay support members further including additional fastening means located on the outer surface portion respectively thereof, said additional fastening means being cooperatively engageable with said coupling means for connecting together said inside and outside stay support members when said members are positioned adjacent the inner and outer surface portions of the leg and foot of the user.

9. The ankle brace defined in claim 8 wherein said lower leg covering portion is comprised of a stretchable yet stiff material.

10. The ankle brace defined in claim 8 wherein the fastening means on the inner surface portion of said inside stay support member includes segments of a material which will adhere to the corresponding means located on said main brace body when engaged therewith.

11. The ankle brace defined in claim 8 wherein the fastening means on the inner surface portion of said outside stay support member includes segments of a material which will adhere to the corresponding means located on said main brace body when engaged therewith.

12. The ankle brace defined in claim 8 wherein the fastening means on the outer surface portion of said inside and outside stay support members includes at least one segment of a material which will adhere to said coupling means when engaged therewith.

* * * * *

UNITED STATES PATENT AND TRADEMARK OFFICE
CERTIFICATE OF CORRECTION

PATENT NO. : 5,393,303
DATED : February 28, 1995
INVENTOR(S) : Katsuaki Shiono

It is certified that error appears in the above-indentified patent and that said Letters Patent is hereby corrected as shown below:

Column 8, line 65, "maimer" should be --manner--.

Signed and Sealed this

Second Day of May, 1995

BRUCE LEHMAN

Attest:

Attesting Officer

Commissioner of Patents and Trademarks